United States Patent

Abelson

[11] Patent Number: 5,959,261
[45] Date of Patent: Sep. 28, 1999

[54] STEREOPHONIC STETHOSCOPE

[76] Inventor: Denis M. Abelson, 1105 Old Gulph Rd., Bryn Mawr, Pa. 19096

[21] Appl. No.: 08/897,755

[22] Filed: Jul. 21, 1997

Related U.S. Application Data

[63] Continuation of application No. 08/600,673, Feb. 13, 1996, Pat. No. 5,650,598.

[51] Int. Cl.⁶ .................................................. A61B 7/02
[52] U.S. Cl. .................................................. 181/131
[58] Field of Search ................... 181/131, 137; 381/67

[56] References Cited

U.S. PATENT DOCUMENTS

| | | | |
|---|---|---|---|
| 1,847,607 | 3/1932 | Hardt | 181/131 |
| 2,209,164 | 7/1940 | Kerr | 181/131 |
| 3,124,211 | 3/1964 | Cefaly | 181/131 |
| 4,706,777 | 11/1987 | Baumberg | 181/131 |
| 4,997,055 | 3/1991 | Grady | 181/131 |

*Primary Examiner*—Khanh Dang

[57] ABSTRACT

A stethoscope provided with two conducting tubes and sound sensors, and two 3-way stopcocks; enabling the sound from one sensor to be conducted to one ear, while that from the second sensor is conducted to the other ear. One of the conducting tubes may be detached when the stethoscope is used for monophonic auscultation.

5 Claims, 3 Drawing Sheets

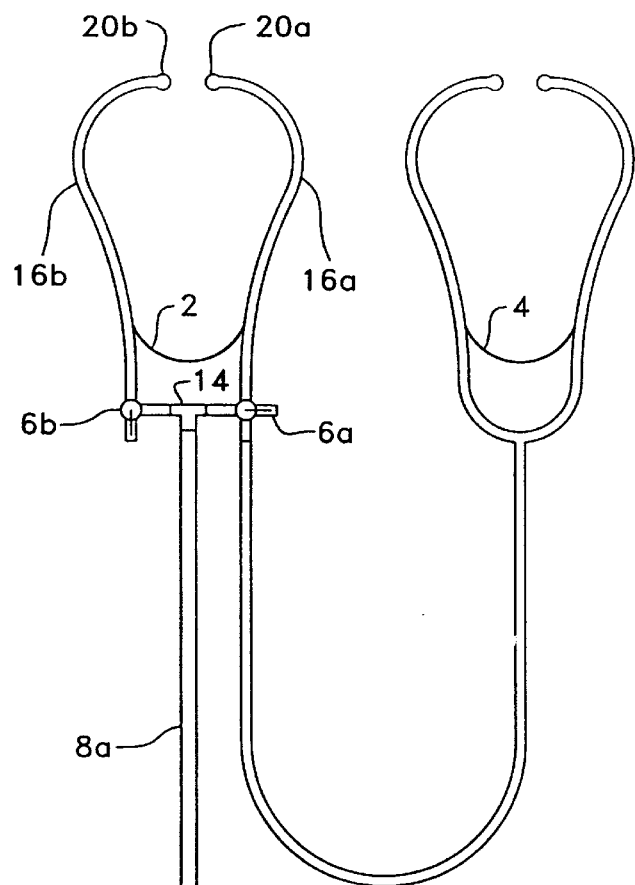
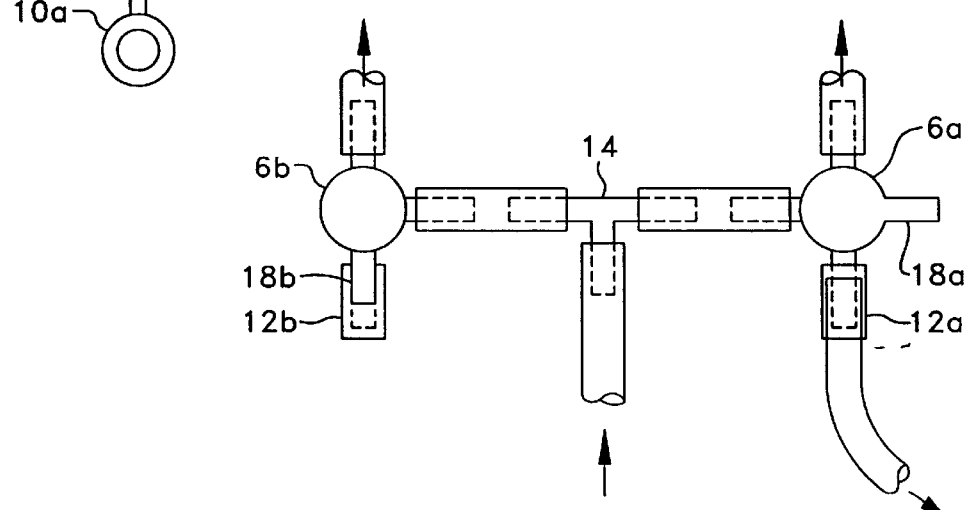
FIG. 3A
FIG. 3B

STEREOPHONIC STETHOSCOPE

This is a continuation of application Ser. No. 08/600,673 filed on Feb. 13, 1996, now U.S. Pat. No. 5,650,598.

BACKGROUND

1. Field of Invention

This invention relates to stethoscopes, specifically to an improved means for monitoring two different sound sources simultaneously.

2. Description of Prior Art

French Patent 558,302 to Scheffler (1923) shows a stethoscope with two sensors or chest-pieces, one connected via a conducting tube to the left ear and the other to the right ear. This device cannot be converted for monophonic listening, i.e., with a single tube and chest-piece; and the user is therefore compelled to have both tubes dangling from his neck at all times. French Patents 580,538 to dePauw (1924), 649,886 to Guery (1928), with addition No. 36,027 (1930), 666,401 to Wilenkin (1929), 715,545 to Hardt (1931), and U.S. Pat. Nos. 1,811,558 to Porter (1931), 1,853,951 to Zala (1932), 2,209,164 to Kerr (1940), 4,706,777 to Baumberg (1987), all suffer from the same disadvantages. The stethoscope shown in U.S. Pat. No. 4,997,055 to Grady (1991) shows a common conducting tube, thus abolishing any possibility of differential or stereophonic auscultation, whereby sounds from two sources such as the lungs can be compared.

SUMMARY OF THE INVENTION

Generally, the invention disclosed herein comprises a stereophonic stethoscope for simultaneously monitoring sound which emanates from different locations on a subject's body. Although embodiments of this invention capable of monitoring sound emanating from more than two different locations may be possible, at least in one embodiment, the invention comprises a stereophonic stethoscope for simultaneously monitoring sound emanating from two different locations on a subject's body. Essentially, the stethoscope comprises two sound sensors: (1) a first sound sensor which detects a first sound which emanates from a first location on the subject's body when the first sensor is substantially in contact with the first location; and (2) a second sound sensor, which detects a second sound which emanates from a second location on the subject's body when the second sensor is substantially in contact with the second location.

Each sound sensor is connected to a sound transmission conductor, such as a conducting tube. Each transmission conductor transmits the sound which is detected by the sensor to which the conductor is attached.

A T-junction having three connection ports is also employed. The conductor for the first sensor is attached to one connection port of the T-junction. The T-junction is then capable of transmitting the sound detected by the first sensor to two stopcocks. The first stopcock is connected to one of the connection ports of the T-junction. The first stopcock may be adjusted to transmit to a first ear piece and ear tip the first sound from the T-junction.

The second stopcock is connected to another of the connection ports of the T-junction. The second stopcock may be adjusted to transmit to a second ear piece and ear tip either: (a) the second sound without transmitting the first sound; or (b) the first sound without transmitting the second sound.

The sound directed from each of the stopcocks is transmitted through each respective ear piece. Each sound then reaches the respective ears of the user of the stethoscope through the ear tips.

In another embodiment of the invention, a teaching binaural may be attached to the first stopcock such that a second user of the stethoscope, such as a student, may simultaneously hear the sound heard by the first user. In other embodiments of the invention, the sound transmission conductors and/or the teaching binaural may also optionally be removably attached to the stopcocks.

The objects and advantages of my invention are:

(a) To provide a stethoscope with two sound sensors which can be used for either monophonic or stereophonic purposes;

(b) To provide a stethoscope in which one conducting tube can easily be detached and stored in the clinician's pocket, permitting the stethoscope to be used if desired as a monophonic instrument with a single sensor;

(c) To provide a stethoscope in which an additional teaching binaural can be attached when required to one of the two 3-way stopcocks, permitting a student to auscultate the heart, lungs, blood vessels, abdomen or other part of the body at the same time as the physician;

(d) To provide a stethoscope in which the two sensors can be of the bell or diaphragm type;

Further objects and advantages will become apparent from a consideration of the ensuing description and drawings.

DRAWING FIGURES

In the drawings, closely related figures have the same number but different alphabetic suffices.

FIG. 3A shows a second embodiment of the stethoscope with the teaching binaural connected.

FIG. 3B is a section view of the 3-way stopcocks in the monophonic mode with the teaching binaural attached.

REFERENCE NUMERALS IN DRAWINGS

| | |
|---|---|
| 2 main binaural | 12 connectors |
| 4 teaching binaural | 14 T-junction |
| 6 3-way stopcock | 16 ear pieces |
| 8 sound conducting tubes | 18 levers |
| 10 sound sensor (diaphragm or bell) | 20 ear tips |

DETAILED DESCRIPTION

Figures 1A, 1B:
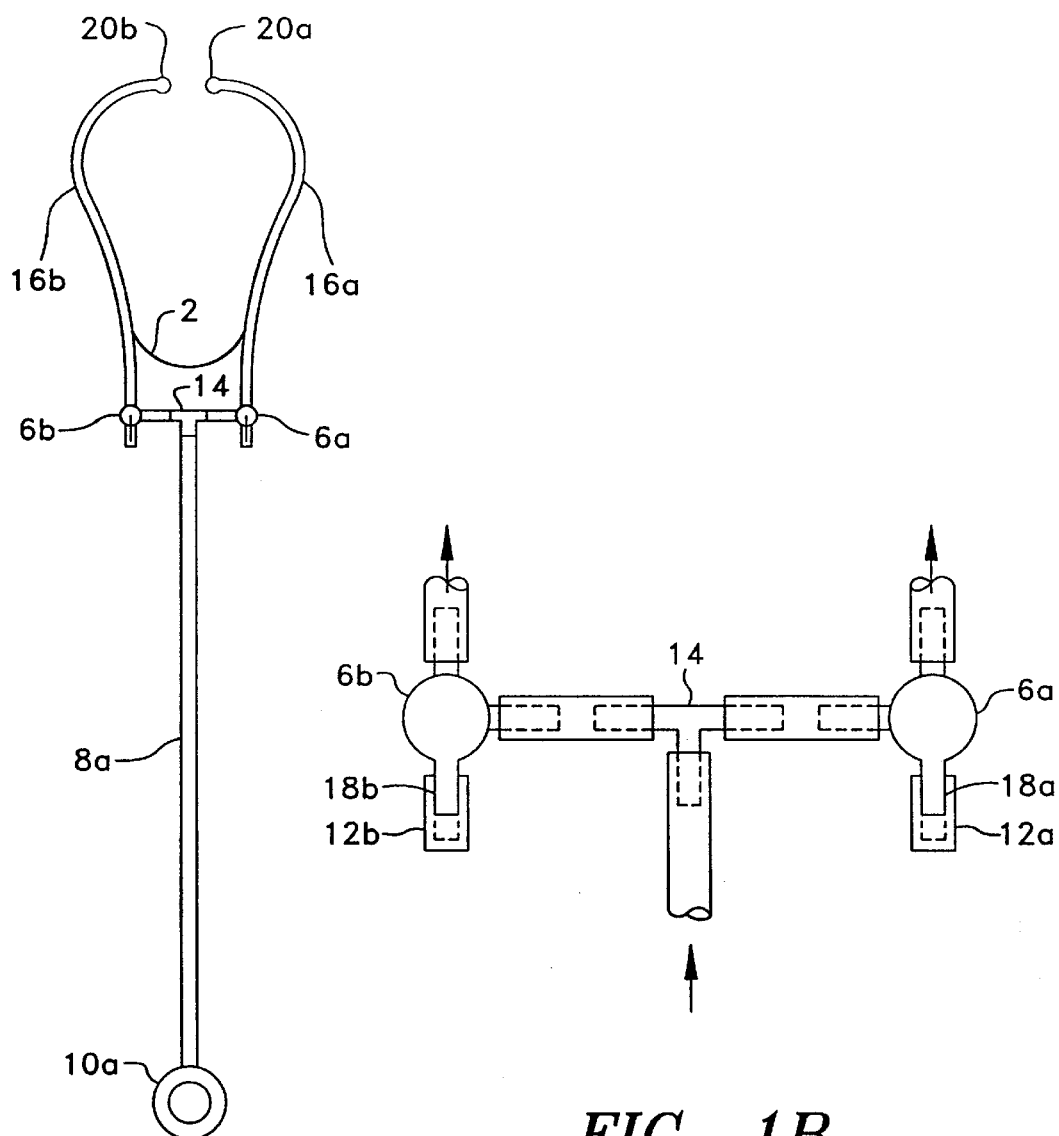
FIG. 1A shows a plan view of a stereophonic stethoscope of the invention, connected for monophonic auscultation.
FIG. 1B is a section view of the 3-way stopcocks in the monophonic mode. The position of the lever indicates the direction in which there is no air channel, therefore no possibility of sound transmission.

A typical embodiment of the stereophonic stethoscope of the present invention is illustrated in FIG. 1A. In the monophonic mode a sound receiving sensor 10, which may be a diaphragm or bell or a combination thereof, is connected to a conducting tube 8a, which transmits the sound equally via a T-junction 14 to the two 3-way stopcocks 6a and 6b, and thence via the ear pieces 16a and 16b of the main binaural 2 to the ear tips 20a and 20b.

FIG. 1B shows the orientation of the 3-way stopcocks 6a and 6b for binaural reception of a monophonic signal from the sensor 10. Reference will be made to these drawings in describing the operation of the invention. Three-way channels are located within the housing of stopcock 6. Levers 18a and 18b are mounted externally on the housing. Turning one or both of levers 18 changes the position of the channels and hence the direction taken by the sound signal. The arrows in FIG. 1B depict the direction in which sound travels from sensor 10 through stopcocks 6a and 6b, through ear pieces 16a and 16b to ear tips 20a and 20b. The position of the stopcocks in the position shown in FIG. 1B shall be referred to herein as the "monophonic mode."

Figures 2A, 2B:
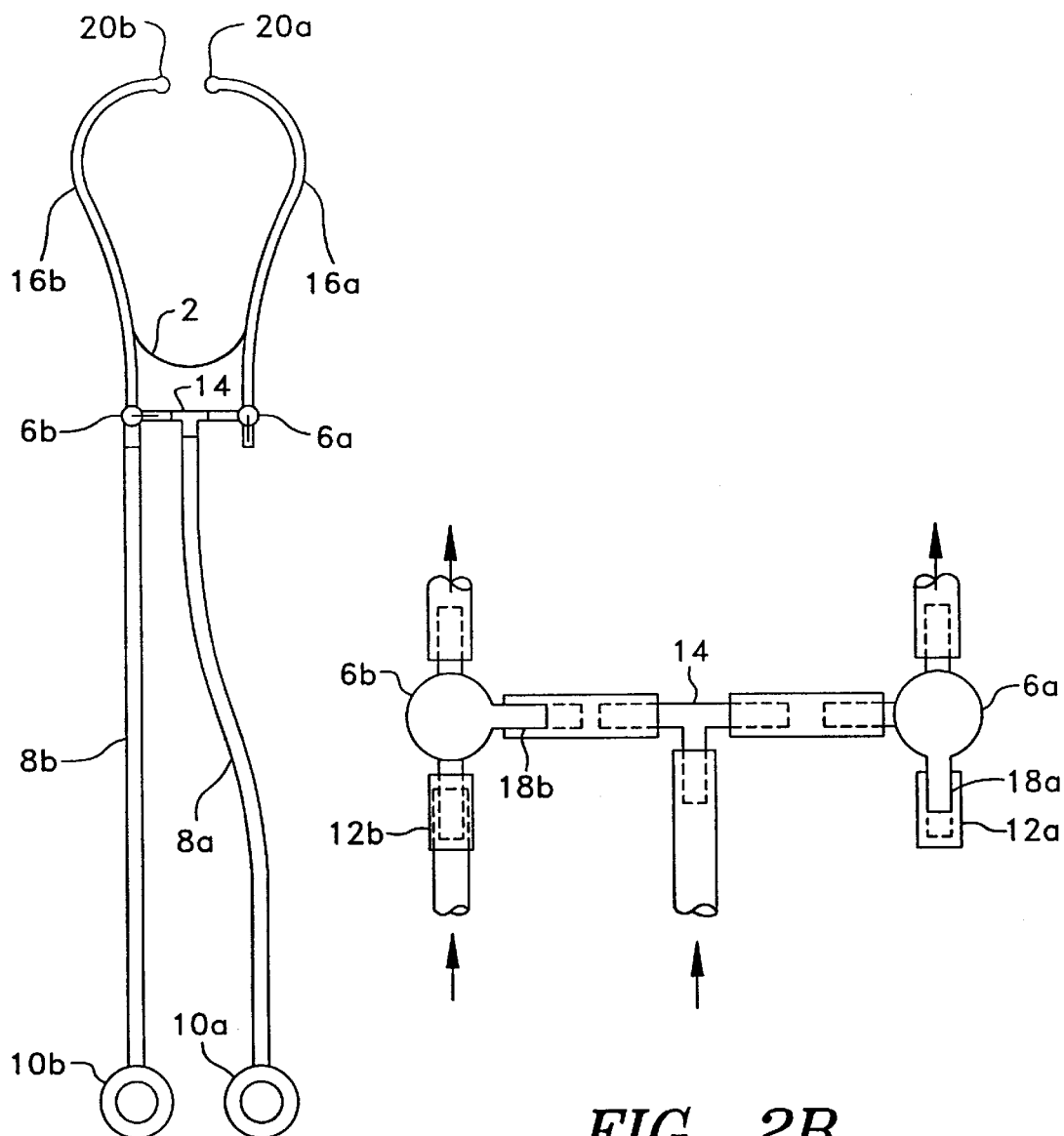
FIG. 2A shows a plan view of the stereophonic stethoscope connected for stereophonic auscultation.
FIG. 2B is a section view of the 3-way stopcocks in the stereophonic mode.

FIG. 2A shows a means of attaching a second conducting tube 8b to stopcock 6b via connector 12b. FIG. 2B shows an enlarged cross-sectional view of the stopcocks in "stereophonic mode." The term "stereophonic mode" as used herein shall mean the position of stopcocks 6a and 6b as shown in FIG. 2B. The arrows in FIG. 2B depict the direction in which sound travels. In stereophonic mode, sound from sensor lob is transmitted to the homolateral ear via ear piece 16b and prevented from traveling via T-junction 14 and ear piece 16a to the controlateral ear. Also, in stereophonic mode, sound from sensor 10a is transmitted to the controlateral ear via ear piece 16a and prevented from traveling via ear piece 16b to the homolateral ear.

An additional embodiment is shown in FIG. 3. In this case a teaching binaural 4 is attached monophonically to stopcock 6a via connector 12a. FIG. 3B shows a cross-sectional view of the stopcocks arranged for monophonic reception by two examining persons of a sound signal from a single sensor. In this position sound from sensor 10a is transmitted to ear pieces 16a and 16b as well as to the ear pieces of teaching binaural 4.

Operation

The manner of using the stethoscope in monophonic mode (see FIG. 1A and 1B) is similar to that for stethoscopes in present use. With stopcocks 6a and 6b in the monophonic mode, sensor 10a is applied to the patient's skin and ear tips 20a and 20b are inserted into the observer's ears.

For stereophonic auscultation a second conducting tube 8b is connected to stopcock 6b, as in FIG. 2A. Stopcocks 6a and 6b are then placed in stereophonic mode (FIG. 2B). Sensors 10a and lob of the same type, either diaphragms or bells, are attached to each of conducting tubes 8a and 8b, and applied to the desired auscultatory sites, such as the right and left carotid arteries in the neck, the femoral arteries in the inguinal regions, the lungs, two different areas of the precordium, or the external nasal orifices (diaphragms only being used here, to avoid transmission of airborne infection from the patient's nose to the observer's ears). In the teaching application (FIG. 3), sound from a single sensor is transmitted via stopcock 6a to teaching binaural 4 as well as to main binaural 2 via stopcocks 6a and 6b.

Ramifications and Scope

Accordingly, the reader will see that the stereophonic stethoscope of this invention can rapidly be switched from monophonic to stereophonic use, and vice versa. Furthermore, the invention:

permits one of the conducting tubes to be detached when the stethoscope is being used in the monophonic mode;

permits an observer to note whether two events, such as the beginning of inspiration over the bases of both lungs, are occurring simultaneously, an observation impossible to make except by stereophonic auscultation;

permits the simultaneous reception of two different sound signals X and Y received from sensors 10a and 10b respectively, in which X may be louder in one ear while Y is louder in the other. For example, over the carotid arteries the sounds of transmitted heart valve closure may be louder on the right side, while a bruit due to turbulent or diminished blood flow is louder on the left. Again, over the bases of the lungs, diminished air entry may be manifest on one side, while rales are audible on the other;

permits an operator to confirm small differences in sound intensity by simply transposing the two sensors, so that the left ear hears signals formerly heard by the right ear, and vice versa;

permits the operator, while holding the sensors on the skin over the carotid or femoral arteries, for example, to distinguish by palpation any differences in the force of the pulse on the two sides of the body.

Although the above description contains several specific applications, these are not intended to limit the scope of the invention, but merely to illustrate some of the preferred embodiments. For example, other types of stopcocks could be employed, the teaching binaural could be modified for stereophonic auscultation using two conducting tubes instead of one, etc., without departing from the spirit of the invention.

Thus the scope of the invention should be determined by the following claims and their equivalents, rather than by the applications described above.

I claim:

1. A stethoscope for simultaneously monitoring sounds which emanate from a sound source, said stethoscope comprising:
    a) a first sound sensor connected to a first sound transmission conductor;
    b) a second sound sensor connected to a second sound transmission conductor;
    c) a junction having multiple sound transmission connections, wherein at least one of said sound transmission connections is connected to at least one of said first and second sound transmission conductors;
    d) a first sound channeling device connected to at least one of said sound transmission connections;
    e) a second sound channeling device connected to at least one of said sound transmission connections, and further connected to at least one of said first and second sound transmission conductors; and
    f) third and fourth sound transmission conductors through which said sounds may be transmitted to the ear of a user, wherein each of said third and fourth sound conductors are connected to at least one of said sound channeling devices.

2. The stethoscope according to claim 1, further comprising fifth and sixth sound transmission conductors wherein said fifth and sixth conductors are connected to at least one of said sound channeling devices.

3. The stethoscope according to claim 2, wherein said fifth and sixth sound transmission conductors comprise a teaching binaural.

4. The stethoscope according to claim 1, wherein at least one of said sound transmission conductors is removably attached.

5. The stethoscope according to claim 2, wherein at least one of said sound transmission conductors is removably attached.

* * * * *